US009012363B2

(12) United States Patent
van Boxtel-Verhoeven et al.

(10) Patent No.: US 9,012,363 B2
(45) Date of Patent: *Apr. 21, 2015

(54) GRANULAR CONTROLLED RELEASE AGROCHEMICAL COMPOSITIONS AND PROCESS FOR THE PREPARATION THEREOF (71) Applicant: Everris International B.V., Heerlen (NL)

(72) Inventors: Lonneke Jacoba van Boxtel-Verhoeven, Born (NL); Johannes Gijsbertus Antonius Terlingen, Landgraaf (NL); Petra Leonarda Hendrica Lunde-Vannuys, Heerlen (NL)

(73) Assignee: Everris International B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/952,187

(22) Filed: Jul. 26, 2013

(65) Prior Publication Data
US 2013/0310255 A1  Nov. 21, 2013

Related U.S. Application Data (63) Continuation of application No. 13/008,771, filed on Jan. 18, 2011, now Pat. No. 8,497,229, which is a continuation of application No. 11/238,376, filed on Sep. 29, 2005, now abandoned.

(51) Int. Cl.
| *A01N 25/26* | (2006.01) |
| *A01N 25/12* | (2006.01) |
| *A01N 25/00* | (2006.01) |
| *A01N 57/10* | (2006.01) |
| *A01N 55/02* | (2006.01) |
| *C05G 3/02* | (2006.01) |
| *A01N 25/14* | (2006.01) |
| *C05G 3/00* | (2006.01) |

(52) U.S. Cl.
CPC ........ *C05G 3/02* (2013.01); *A01N 25/12* (2013.01); *A01N 25/14* (2013.01); *C05G 3/0029* (2013.01); *Y10S 514/951* (2013.01); *Y10S 514/952* (2013.01)

(58) Field of Classification Search
USPC ......... 504/101, 126, 194, 360, 367; 71/64.11; 514/951, 952; 424/417, 420, 490, 493, 424/497
See application file for complete search history.

(56) References Cited

U.S. PATENT DOCUMENTS

| 3,223,518 A | 12/1965 | Hansen |
| 4,062,855 A | 12/1977 | Allan et al. |
| 4,267,280 A | 5/1981 | McCormick |
| 4,435,383 A | 3/1984 | Wysong |
| 4,657,576 A | 4/1987 | Lambie |
| 4,880,455 A | 11/1989 | Blank |
| 4,946,686 A | 8/1990 | McClelland et al. |
| 4,971,796 A | 11/1990 | Sjogren |
| 5,516,520 A | 5/1996 | Yang et al. |
| 5,652,196 A | 7/1997 | Luthra |
| 5,783,203 A | 7/1998 | Baron et al. |
| 5,917,110 A | 6/1999 | Kust |
| 5,938,813 A | 8/1999 | Araya et al. |
| 6,080,221 A | 6/2000 | Moore |
| 6,187,074 B1 | 2/2001 | Von Locquenghien et al. |
| 6,284,278 B1 | 9/2001 | Waldman et al. |
| 6,309,439 B1 | 10/2001 | Von Locquenghien et al. |
| 6,682,751 B1 | 1/2004 | Hargrove et al. |
| 6,693,063 B2 | 2/2004 | Schnabel et al. |
| 6,787,234 B2 | 9/2004 | Tijsma et al. |
| 8,497,229 B2 | 7/2013 | van Boxtel-Verhoeven et al. |
| 2003/0215657 A1 | 11/2003 | Tijsma et al. |
| 2004/0105877 A1 | 6/2004 | Hargrove |

FOREIGN PATENT DOCUMENTS

| EP | 0079668 | 5/1983 |
| EP | 0 305 918 | 3/1989 |
| EP | 0755370 | 10/1995 |
| EP | 0966882 | 1/1998 |

(Continued)

OTHER PUBLICATIONS

International Search Report for International Application No. PCT/US06/037893, mailed May 2, 2008.
Written Opinion for International Application No. PCT/US06/037893, mailed May 2, 2008.
Supplementary European Search Report for corresponding European Application No. EP 06 81 5700, mailed Mar. 16, 2010.
Canadian Office Action issued in corresponding Canadian Application No. 2,623,740 on Aug. 31, 2011.
Nasser, W.; "Waxes, Natural and Synthetic;" McKetta, John J., Encyclopedia of Chemical Processing and Design, vol. 67; 1999; ISBN: 0-8247-2618-9.
Polyethylene-block-poly(ethylene glycol) Material Safety Data Sheet, 2012, Sigma-Aldrich, Version 5.0, 6 pages.

(Continued)

Primary Examiner — Sue Liu
Assistant Examiner — Andriae M Holt
(74) Attorney, Agent, or Firm — Hunton & Williams LLP (57) ABSTRACT A granular agrochemical composition is disclosed including a granular core material having a water soluble portion with a first coating layer applied on the surface of the core material and a second coating layer applied on the surface of the first coating layer. The first coating layer includes a wax composition having a biologically active ingredient incorporated therein and the second coating layer includes a polymeric composition. The granular agrochemical composition exhibits a controlled rate of release of the biologically active ingredient therefrom over a period greater than about 30 days from the date of initial exposure of the granular composition to moisture whereby essentially all of the biologically active ingredient incorporated in the wax material of the first coating layer is released from the granular composition before the water soluble portion of the granular core material is released from the granular composition.

21 Claims, 3 Drawing Sheets (56) References Cited

FOREIGN PATENT DOCUMENTS

| | | |
|---|---|---|
| EP | 1063215 | 12/2000 |
| EP | 1148107 | 10/2001 |
| JP | 50-021989 | 3/1975 |
| JP | 03-60486 | 3/1991 |
| JP | 03-060486 | 3/1991 |
| JP | 06-009304 | 1/1994 |
| JP | 06-072805 | 3/1994 |
| JP | 08-151286 | 6/1996 |
| JP | 2001-005002 | 1/2001 |
| WO | WO 95-28370 | 10/1995 |
| WO | WO 95/34200 | 12/1995 |
| WO | WO 99/07654 | 2/1999 |
| WO | WO 02/05641 | 1/2002 |
| WO | WO 2007/041234 | 4/2007 |

OTHER PUBLICATIONS

Extended European Search Report for corresponding European Application No. EP 12177258, mailed May 3, 2013.
Communication Pursuant to Article 94(3) for corresponding European Application No. EP 06 81 5700, mailed Apr. 2, 2013.
Chinese Office Action for Chinese Patent Application No. 200680044762.5 mailed Feb. 14, 2014—English translation and Chinese Office Action, 10 pages.

GRANULAR CONTROLLED RELEASE AGROCHEMICAL COMPOSITIONS AND PROCESS FOR THE PREPARATION THEREOF

CROSS-REFERENCE TO RELATED APPLICATIONS

This application is a continuation of U.S. application Ser. No. 13/008,771, filed on Jan. 18, 2011, which is a continuation of U.S. application Ser. No. 11/238,376, filed on Sep. 29, 2005, now abandoned.

BACKGROUND OF THE INVENTION

1. Field of the Invention

The present invention relates to granular agrochemical compositions and to processes for producing such compositions. More particularly, it relates to controlled release agrochemical compositions having a first coating layer comprising a wax composition with a biologically active ingredient incorporated therein applied on the surface of a core material and having a second coating layer comprising a polymeric composition applied on the surface of the first coating layer and to processes for preparing such compositions.

2. Description of Related Art

Agrochemicals as referred to herein include biologically active ingredients/plant protection products such as insecticides, herbicides, fertilizers, growth regulators, pheromones, biostimulants, acaricides, miticides, nematocides, fungicides and the like. Such agrochemicals are well known and are in common usage for controlling pests and diseases and for promoting plant growth in agriculture. In practice, it is important to make a sufficient amount of such agrochemical or active ingredient available to the biological system in order to control pests or disease or to promote growth. Too much active ingredient, however, is inefficient and not desired because of environmental and economic concerns. Furthermore, higher amounts of active ingredient lead to increased risks of leaching to ground water or surface water. Higher amounts can also lead to phytotoxicity for the crop. Insufficient levels of active ingredients results in lack of control of the pest and increase the risk of resistance.

Thus, it is generally known that it is important to deliver the correct amount of active ingredient to the crop for control of the pest or disease and to promote growth over a given period of time. However, multiple applications of active ingredients becomes labor and cost intensive. With conventional applications of liquid or powder formulations, relatively high amounts of active ingredients are applied several times to assure control of pests over a longer period of time, typically 3-6 times for seasonal control, and users are exposed to the active ingredients during each application, which is undesirable.

When active ingredients are applied in granular form instead of by spraying or dusting, the risk of exposure to the active ingredient is more limited. After application of a granular pesticide the active ingredient is released to the soil under the influence of water. The release rate varies depending on the formulation of the granule. The granules can be divided into two categories. The first category releases the active ingredient quickly and has to be applied several times during the season. The second category releases the active ingredient over a period of time and provides control of pests during an extended period up to a whole season. To control pests over a longer period of time the concentration of active ingredient must be above the minimal effective level during the whole period. To maintain this effective concentration, the loss of active ingredient via leaching, degradation and uptake by the plant must be compensated. The rate of degradation and leaching depends on the active ingredient and the amount that is lost, is directly related to the concentration of the active ingredient in the soil. Thus high concentrations result in relatively more degradation and leaching.

In general, known controlled release granular active ingredients suffer serious limitations. They generally do not deliver the active ingredient to the biological system for periods of greater than about 30 days from the date of initial exposure to moisture and/or they do not completely release the active ingredient. The practical limitations of systems that release the active ingredient in less than about 30 days are that they must be periodically reapplied during the growing season resulting in additional cost. The limitations of systems which do not completely release the active ingredient in the desired period of time are related to efficiency. More active ingredient must be used to compensate for the portion which does not release effectively. This incurs additional cost to the user. Furthermore, the residual, unreleased active ingredient poses an environmental threat and can lead to biological resistance in the pest. Active ingredient that is not released cannot be used for controlling a pest or disease and will give undesirable residues of active ingredient. In the long run this can lead to build up of chemicals in soil and this is even less desirable. Without residues after the release period soil can be recycled without any risk for succeeding crop. The use of lower amounts of active ingredients and high efficiency are especially desired from an economical and environmental point of view.

A number of approaches have been taken heretofore in production of controlled release granular agrochemical compositions. For example, EP Patent 079668 discloses an encapsulated pesticide product wherein a granular core is coated with a pesticide and then a plurality of layers of a membrane like coating are applied over the pesticidal coat to enable controlled release of such pesticide over a period of time upon contact with water. However, the products disclosed in EP Patent 079668 are structurally distinct from the products of the present invention and, accordingly, disadvantageously fail to exhibit a controlled rate of release of the pesticide over a period greater than about 30 days from the date of initial exposure of the product to moisture in a manner such that essentially all of the pesticide coated on the core is released from the granular composition before the water soluble portion of the core material is released from the product as is achieved with the compositions of the present invention.

U.S. Pat. No. 6,682,751 discloses a granular pesticide comprising a core material coated with an inner polymer membrane formed in-situ on the core material with a pesticide applied to the inner polymer membrane and an outer controlled release polymer membrane formed in situ on the pesticide to permit controlled release. The pesticide may be incorporated in several "sandwich" layers. Again, the products of U.S. Pat. No. 6,682,751, are structurally different from the products of the present invention and fail to exhibit a controlled rate of release of the pesticide over a period greater than about 30 days from the date of initial exposure of the product to moisture in a manner such that essentially all of the pesticide coated on the core is released from the granular composition before the water soluble portion of the core material is released from the product.

U.S. Pat. No. 6,080,221 discloses the coating of porous surfaces of fertilizer particles with tenacious pesticide-resin solids to form attrition resistant fertilizer-pesticide combination particles. In this disclosure, the pesticide is dispersed in a resinoid matrix, which is subsequently bonded onto and into the fertilizer surface. Patent U.S. Pat. No. 4,971,796 describes another slow release granular product in which the pesticide is matrixed into the coating. The granule comprises one layer of proteinacious material or more layers of proteinacious material with intermediate spacing layers. The active ingredient is in the proteinacious layer and is released when this layer degrades. The release rate is changed by varying the cross linking or the thickness of the layer. The products of U.S. Pat. Nos. 6,080,221 and 4,971,796 fail to exhibit a controlled rate of release of the pesticide over a period greater than about 30 days from the date of initial exposure of the product to moisture in a manner such that essentially all of the pesticide coated on the core is released from the granular composition before the core material is released from the product.

U.S. Pat. Nos. 6,187,074 and 6,309,439 disclose a fertilizer coated with a carboxyl-carrying ethylene copolymer, the carboxyl-carrying ethylene copolymer being composed of 75%-90% by weight ethylene and from 10%-25% by weight of an alpha-olefinically unsaturated C3-C8 carboxylic acid. The coated fertilizer particles specifically do not contain any crop protection chemicals. Thus, the products disclosed in these patents fail to exhibit a controlled rate of release of the pesticide over a period greater than about 30 days from the date of initial exposure of the product to moisture in a manner such that essentially all of the pesticide coated on the core is released from the granular composition before the core material is released from the product.

U.S. Pat. No. 6,693,063 discloses products that are structurally distinct from the present compositions teaching wax microcapsules and wax dispersion of pesticides in the absence of a water soluble core material. Other encapsulated pesticides which do not include water soluble core materials are disclosed in Japanese Examined Patent Publication JP-B 5002/1989, JP-A 9304/1994 and JP-A 72805/1994.

Other pesticides displaying matrix release systems are disclosed in. U.S. Pat. No. 4,435,383 wherein solid controlled release pesticidal products are formed comprising an active ingredient incorporated in a homogeneous combination with a polymer by melting the polymer and mixing it with the active ingredient. During this process additional cross-linking agent are added. Another matrix based pesticide is disclosed in U.S. Pat. No. 5,516,520 wherein a pesticidally active ingredient is encapsulated in a starch-borax-urea matrix. The slow release from this matrix is limited to oil-soluble pesticides. The release rate is changed by varying the amount of urea.

EP Patent 0755370 discloses other matrix release products which are mixtures of a nitromethylene or related substances with fertilizers and glue. EP Patent 1063215 describes briquettes that slowly release active ingredients. The slow release is obtained via absorption or adsorption of the active ingredient onto solids with high surface area.

The matrix systems all demonstrate release mechanisms wherein the release of active ingredients from the matrix systems is via desorption from an absorped state or by diffusion and not by an osmotic (pump) release mechanism as employed herein. The release rate of such matrix systems depends on the concentration of the active ingredient in the system. Thus, the release rate of such granules decreases over time resulting in initial fast release of active ingredients which provides high amounts of active ingredient in the soil at the start, and a slow release at the end.

Other types of agrochemical products that can release an active ingredient over a period of time are biodegradable systems such as those disclosed in U.S. Pat. No. 4,062,855 wherein active ingredients are incorporated into a polymer that are released via biodegradation. U.S. Pat. No. 4,267,280 describes a product that has a biodegradable polymer system that contains the pesticide. It releases the pesticide depending on environmental conditions via hydrolyses or depolymerization.

A disadvantage of these biodegradable products is that the release of active ingredient depends on the speed of degradation of the polymer and this degradation depends on the activity of ambient microorganisms. The activity of the microorganisms can vary greatly depending on the soil type and local environmental conditions, types of microbes, pH, temperature, moisture and the like. Thus, the release rate of active ingredients varies and it is difficult to match the release precisely with the minimal required active ingredient concentrations.

Other coated granular pesticidal compositions are disclosed in International Patent Publication WO 02/05641 wherein a pesticidal composition is disclosed that can slowly release an active ingredient. That publication discloses the preparation of several granular materials with different numbers of coating layers or properties of the coating layers. Each of the granular materials has its own release profile. By blending the different granules they can obtain the desired release pattern of the product. The variation of release is purely based on coating properties and not on solubility of components in the formulation.

EP Patent 0966882 discloses a controlled release granular product wherein only single granules exhibit a delay of release after which the pesticide is released. Thus, after a period of time, a particular granule breaks open and delivers a portion of active ingredient to the environment. The release over a period of time is established by combining multiple 'delayed-release' granules, which all have different delay times. The granules themselves do not exhibit controlled release properties, only a delayed release.

EP Patent 1148107 discloses a coating procedure for granules with a low content of volatile substances. This coating procedure ensures that the release function of the granules does not change in two weeks time.

Another example of formulations of this general type is disclosed in International Patent Publication WO 99/07654 comprising encapsulated fertilizers with a polymeric envelope that contains a hormone (e.g. an auxin or cytokinine). The hormone is mixed with a monomer that form a polymeric envelope. Again, the products disclosed in this reference do not exhibit a controlled rate of release of the pesticide over a period greater than about 30 days from the date of initial exposure of the product to moisture in a manner such that essentially all of the pesticide coated on the core is released from the granular composition before the core material is released from the product.

In view of the benefits that can be derived from agrochemical compositions that provide controlled release of active ingredients including efficiency and economy of use of the active ingredients, the reduced environmental impact achieved, the ability to employ a single application of the composition for extended control of pests and diseases, reduction in user exposure to the compositions, it is clear that new, more technically advanced agrochemical products would be highly desirable. In particular, a desired objective is to provide agrochemical compositions that provide extended useful life with essentially complete release of an active ingredient occurring over a periods of greater than about 30 days from the date of initial exposure to moisture.

Thus, prior art agrochemical compositions have fallen short in providing desired functionality and the present invention is intended to overcome such problem by providing compositions which functionally demonstrate a controlled rate of release of the active ingredient over a period of time greater than about 30 days from the date of initial exposure of the compositions to moisture in a manner such that essentially all of the active ingredient coated on the core is released from the granular composition before the core material is released from the product.

BRIEF SUMMARY OF THE INVENTION

The present invention relates to granular agrochemical compositions which exhibit functionality wherein essentially complete release of the active ingredients occurs over a period of time greater than about 30 days. These granular compositions comprise a granular core material which, preferably, is at least partially water soluble, coated with a first coating layer comprising a wax material having a biologically active plant protection product or active ingredient incorporated therein and having a second coating layer comprising a polymeric composition applied on the surface of the first coating layer.

The present invention involves the development of a new system for release of active ingredients, such as herbicides, growth regulators, pheromones, bactericides, insecticides, acaricides and fungicides and the like, over a defined period of time with high efficiency.

In a preferred embodiment, the granular agrochemical composition of the present invention exhibit a controlled rate of release of the biologically active ingredient therefrom over a period greater than about 30 days from the date of initial exposure of the granular composition to moisture whereby essentially all of the biologically active ingredient incorporated in the wax material of the first coating layer is released from the granular composition while at least a residual amount of the core material remains in the granular composition. In this regard, it has been found that the release rate of the compositions can be influenced by changing the coating properties, the solubility of the core-material and by adjusting various others of the product constituents.

DETAILED DESCRIPTION OF THE INVENTION

The products of the present invention comprise granular agrochemical compositions including a granular core material having a first coating layer applied on the surface of the core material and a second coating layer applied over the surface of the first coating layer. The first coating layer comprises a wax material having a plant protection product incorporated therein and the second coating layer comprising a polymeric composition.

The granular composition of this invention exhibit a controlled rate of release of a plant protection product therefrom over a period greater than about 30 days from the date of initial exposure of the granular composition to moisture, preferably up to about 104 weeks after initial exposure to moisture, whereby essentially all of the plant protection product incorporated in the wax material of the first layer is released from the granular composition while at least a residual amount of the water soluble core material remains in the granular composition and methods to make such a granular agrochemical composition.

Thus, the present compositions enable lower application rates for the same period of control because the plant protection products is essentially completely released at a control rate over a period of greater than 30 days, preferably up to about 104 weeks, from the date of initial exposure to water. The products of this invention have a high efficiency. This means that essentially all of the active ingredient, preferably greater than 90% of the initial weight of the active ingredient in the wax coating layer is released to the environment before the water soluble content of the core material is completely depleted.

The process for preparing the granular compositions of the present invention which exhibit essentially complete release of the active ingredient over a period greater than about 30 days, preferably comprises coating a core material with a first coating layer comprising a wax material having a biologically active ingredient incorporated therein and applying a second coating layer comprising a polymeric composition applied over the surface of the first coating layer.

Most preferably, the core material is at least partially water soluble ensuring transport of water to the granule through the first and second coating layers via osmosis. The "osmotic" transport of the ingredients occurs as a result of the pumping of water into and a solution out of the granule and continues until all core material has been released. Accordingly, once dissolved, the water dissolvable core material as well as the biologically active ingredient in the first coating layer are transported out of the granule.

Exemplary of suitable core materials for use herein are fertilizers such as ammonium sulfate, potassium nitrate, potassium sulfate, urea, ammonium nitrate, monopotassium sulfate, ammonium phosphate, super-phosphate, calcium phosphates, potassium phosphate, potassium chloride, magnesium oxide, magnesium sulfate, dolomite and the like or any fertilizers obtained from compounding a mixture of these fertilizers. Also, non-active materials such as sugar and other granular materials may be employed as the core material herein, if desired.

In a preferred embodiment of this invention, the core materials comprise at least one secondary nutrient and/or micronutrient. Suitable secondary nutrients include calcium, magnesium, sulfur and mixtures thereof. Suitable micronutrients, in chelated or non-chelated form, include iron copper, zinc, manganese, boron, cobalt, chlorine, sodium, molybdenum and mixtures thereof.

With regard to the wax composition to be employed to form the first coating layer, in a most preferred embodiment of this invention, the wax should be water soluble to facilitate an even better dissolution of the active ingredient in the coating layer.

The granular agrochemical composition of the present invention exhibits a controlled rate of release of a plant protection product (active ingredient) therefrom over a period greater than about 30 days from the date of initial exposure of the granular composition to moisture whereby essentially all of the plant protection product incorporated in the wax material of the first layer is released from the granular composition while at least a residual amount of the water soluble core material remains in the granular composition.

Exemplary, of suitable biologically active ingredients for use herein are pesticides, insecticides, herbicides, fungicides, fertilizers, growth regulators, pheromones, biostimulants, acaricides, miticides, nematocides and mixtures thereof.

For example, one or more suitable herbicides for use herein include dichlorophenoxyacetic acid, dichloropicolinic acid, dichloro-o-anisic acid, diquation, phosphonomethyl)glycine, isopropyl-4-methyl-5-oxo-2-imidazolin-2-YL)-nicotinic acid, methyl 2-(((((4-methoxy-6-methyl-1,3,5-triazin-2-YL) amino)carbonyl)amino)sulfonyl)benzoate, butyl-4-(2,4-dichloro-5-isopropoxyphenyl-delta2-1,3,4-oxadiazoline-5-one (Note: delta2=delta superscript 2), ethylpropyl)-3,4-dimethyl-2,6-dinitrobenzenamine, ehtyl 2-chloro-5-4-chloro-(5-difluoromethoxy)-1-methyl-1H-pyrazol-3-YLY-4-fluorophenoxyacetate(CAS name), dichloro-8-quinolinecarboxylic acid, trichloro-2-pyridinyloxyacetic acid, glyphosate, glufosinate-ammonium, derivatives of phenoxyacetic acid, phenoxypropionic acid, phenoxybutyric acid, 4-amino-3,5,6-trichloro-picolinic acid, phenoxyethyl sulphuric acid, halogeneated benzoic acid, halogenated acetic acid, halogenated propionic acid, phenylurea, or bipyridylium, and certain mineral salts of sodium chlorate, sodium or potassium 2,4-dichlorophenoxyacetate, sodium or potassium 4-chloro-2-methylphenoxyacetate, sodium or potassium 2,4,5-trichlorophenoxyacetate, sodium or potassium 2-(4-chloro-2-methylphenoxy)-propionate, sodium or potassium 2-(2,4-dichlorophenoxy)-propionate, sodium or potassium 4-(2,4-dichlorophenoxy)-butyrate, sodium or potassium 4-(4-chloro-2-methylphenoxy)-butyrate, sodium or potassium 4-(2,4,5-trichlorophenoxy)-butyrate, sodium or potassium 4-amino-3,5,6-trichloropicolinate, sodium 2-(2,4-dichlorophenoxy)-ethylsulfate, 2,3,6-trichlorobenzoic acid, 3,6-dichloro-2-methoxybenzoic acid, sodium chloracetate, trichloracetic acid, sodium 2,2-dichloropropionate, sodium 2,2,3-trichloropropionate, N,N-dimethyl-N'-phenyl urea and its trichloracetic salt, the trichloracetate of N,N-dimethyl-N'-(4-chlorophenyl) urea, copper suphate, iron sulphate, 1,1'-dimethyl-4,4'-bipyridylium dichloride, 1,1'-bis(3,5-dimethyl-4-morpholinyl)-carbonylmethyl-4,4'-bipyridylium dichloride, 9,10-dihydro-8a, 10a-diazaphenanthrene dibromide, 3-amino-1,2,4-triazole, symmetrical triazines and the like.

Suitable insecticides include one or more of the following: dimethyl acetylphosphoramidothioate; ethanimidamide, N-{(6-chloro-3-pyridinyl)methyl}-N'-cyano-N-methyl-,(E)-(90) (CA Index name); hydrazinecarboxylic acid, 2-(4-methoxy{1,1'-biphenyl}-3-YL)-, 1-methylethyl ester (9Cl) (CA Index Name); methyl{1,1'-biphenyl}-3-YL)methyl 3-(2-chloro-3,3,3-trifluoro-1-propenyl)-2,2-dimethylcyclopropanecarboxylate, {1.alpha.,3.alpha.(Z)}-(.+-.)-; naphthyl-n-methylcarbamate; pyrrole-3-carbonitrile, 4-bromo-2-(4-chlorophenyl)-1-(ethoxymethyl)-5-(trifluoromethyl); chloro-alpha-(1-methylethyl)benzeneacetic acid, cyano(3-phenoxyphenyl)methyl ester amino-1-(2,6-dichloro-4-(trifluoromethyl)phenyl)-4-(1,R,S)-(trifluoromethyl)sulfinyl)-1H-pyrazole-3-carbonitrile; benzoic acid, 4-chloro-, 2-benzoyl-2-(1,1-dimethylethyl)hydrazide (9Cl) (CA Index Name); pyrethrins; deoxy-2,3,4-tri-o-methyl-alpha-L-mannopyranosyl)oxy)-13-{{5-(dimethylamino)tetrahydro-??methyl-2H-pyran-2-YL}oxy}-9-ethyl-2,3,3A,5A,5B,6,9,10,11,12,13,14,16A,16B-tetradecahydro-14-methyl-1H-as-indaceno{3,2-D}oxacyclododecin-7,15-dione,(cont'd qual; oxadiazin-4-imine, 3-(2-chloro-5-thiazolyl)methylytetrahydro-5-methyl-N-nitro-(9Cl) and the like.

Suitable fungicides for use in the present invention include tetrachloroisophthalonitrile; ethoxy-3-(trichloromethyl)-1,2,4-thiadiazole; dichlorophenyl)-4-propyl-1,3-dioxolan-2-YL)methyl)-1H-1,2,4-triazole; carbamic acid, 2-1-(4-chlorophenyl)-1H-pyrazol-3-yloxyymethylyphenylymethoxymethyl ester (CAS name); dimethyl ((1,2-phenylene)bis (iminocarbonothioyl))bis(carbamate) and the like.

Suitable plant growth regulators for use in the present invention include RS,3RS)-1-(4-chlorophenyl)-4,4-dimethyl-2-(1H-1,2,4-triazol-1-YL)pentan-3-OL; cyclohexanecarboxylic acid, 4-(cyclopropylhydroxymethylene)-3,5-dioxo-,ethyl ester.

Other examples of biologically active ingredients which may be employed in preparing the granular compositions of this invention include (z)-11-tetradecenyl acetate; 1,2-benzisothiazolin-3-on; 1,2-Dibromoethane; 1,3-dichloro-5,5-dimethylhydantoine; 1,3-dichloro-5-ethyl-5-methylhydantoine; 1-bromo-3-chloro-5,5-dimethylhydantoine; 1-Chloro-2,3-epoxyethane; 1-methylcyclopropene;1-naftylacetamide; 1-naftylacetic acid; 2-(thiocyanomethylthio)benzothiazole; 2,2 dibromo-3-nitrilopropionamide; 2,T-Bipyridyl; 2,2-dithiobisbenzamide; 2,4,5-T, 2,4-D, 2,4-DB; 2,4-Dichloroanisole; 2,4-Dichlorobenzoic acid; 2,4-Dichlorophenol; 2,6-Dichlorophenol; 2-Aminopyridine; 2-bromo-2-nitro-1,3-propanediol; 2-bromo-4-hydroxyacetofenon; 2-phenylfenol; 2-methyl-4-isothiazolin-3-on; 2-methylthio-4-tert. butylamino-cyclopropylamino-s-triazine; 3-indolylacetic acid; 4,4'-Bipyridyl; 4,6-Dichloro-2-methylphenoxyacetic acid; 4,6-Dichloro-o-cresol; 4,6-Dichloro-o-tolyloxyacetic acid; 4-chloro-2-benzylfenol; 4-chloro-3-methyl-sodiumfenolate; 4-Chloro-m-cresol; 4-Chloro-o-cresol; 5-chloro-2-methyl-4-isothiazolin-3-on; 5-oxo-3,4-dichloro-1,2-dithiol; 6-Chloro-2-methylphenoxyacetic acid; 6-Chloro-o-tolyloxyacetic acid; 6-Chloro-p-cresol; abamectine; Acephate; acetamiprid; aclonifen; Alachlor; Aldicarb; Aldrin; alkylarylpolyglycolether; alkyldimethylbenzylammoniumchloride; alkyldimethylethylbenzylammoniumchloride; alkyltrimethylammoniumchloride; alpha-Cypermethrin; alpha-Cypermethrin; aluminium-phosphide; aluminiumsulfate; Ametryn; amfotensides; Amidate; amidosulfuron; Aminocarb; Amitraz; Amitrole; ammoniumbichromate; ammoniumbifluoride; ancymidol; Anilazine; arsenepentoxide; Asulam; Atrazine; auxin; azaconazole; azadirachtine-a; azamethifos; Azinphosmethyl; azocyclotin; azoxystrobin; bariummetaborate; amber acid dialdehyde; beauveria bassiana; benazolin-ethyl; Bendiocarb; Benfluralin; Benfuracarb; Benomyl; Bensulfuron-methyl; Bensultap; Bentazone; benthiavalicarb-isopropyl; Benzoylprop-ethyl; benzyladenine; benzylbenzoate; beta-Cyfluthrin; BHTO; bifenazate; Bifenox; bifenthrin; Binapacryl; Bioallethrin; Bis(ethylenediamine) copper; Bitertanol; bitumen; borate; Borax; boric acid; boscalid; Brodifacoum; Bromacil; Bromadiolone; Bromocresol green; Bromophenol blue; Bromophos; Bromothymol blue; Bromoxynil; bromuconazole; bromo-chloro-5,5-dimethylhydantoine mixtures; bromofenoxim; bromonitrostyrene; bromopropylate; buminafos; bupirimate; buprofezin; Butachlor; butocarboxim; butoxycarboxim; Butylate; Butyl-magnesium chloride; calciumcyanide; calciumhypochlorite; Captan; carbaryl; carbeetamide; Carbendazim; carbendosulf; Carbetamide; Carbofuran; Carbon disulphide; Carbosulfan; carboxin; carfentrazone-ethyl; Cartap; Cetylpyridinium bromide; Chinomethionat; chlofentezin; Chloramben; Chlordimeform; chlordioxide; chlorfacinon; chlorfenoxyacetic acid; Chlorfenvinphos; Chloridazon; Chlormequat; Chlorobenzilate; chlorobromuron; chlorodecone; Chloropropylate; Chlorothalonil; chlorotoluron; Chloroxuron; Chlorphoxim; Chlorpropham; Chlorpyrifos; Chlorsulfuron; Chlorthal; cinidon-ethyl; cis-dichloropropene; clodinafop-propargyl; Clofentezine; clomazone; clopyralid; codlemon; Congo red; coniothyrium minitans; Copper; Copper ethylenediamine sulphate; copper(i)oxide; copper(ii)carbonatehydroxide; copper(ii)oxide; copperhydroxide; coppernaftenate; copperoxychinolate; copperoxychloride; copperresinate; coppersilicofluoride; coppersulfate; copperthiocyanate; Coumatetralyl; Cyanazine; hydrocyanic acid; cyazofamid; Cycloate; Cycloxydim; cyfenothrin; Cyfluthrin; Cyhexatin; Cymoxanil; Cypermethrin; Cyproconazole; cyprodinil; cyromazin; Dalapon; d-allethrin; daminozide; dazomet; DDT; Deltamethrin; d-empenthrin; Deschlorophosphamidon; desmedifam; Desmetryn; d-fenothrin; dialkyldimethylammoniumchloride; Diazinon; Diazomethane; Dicamba; Dichlobenil; dichlofenthion; Dichlofluanid; dichloran; Dichlorodifluoromethane; dichloropropene; Dichlorprop; Dichlorvos; Diclofop; Dicofol; didecyldimethylammoniumchloride; Dieldrin; dienochlor; diethofencarb; diethyl-m-toluamide; difenacum; difenoconazole; difethialon; Diflubenzuron; Diflufenican; Dimedone derivative; Dimercury dicyanide; dimethenamide;Dimethoate; Dimethomorph; Dimethyl sulphate; disodium octaborate; disodiumcyanodithioimidocarbonate; dinoseb; Dinoterb; Dioxane; Diquat; Diquat dibromide; Disulfoton; Dithianon; dithiocarbamate; Dithizone; diuron; d-karvon; dnoc; dodecyldihydroxyethylbenzylammoniumchloride; dodemorf; Dodine; d-tetramethrin; d-trans-Allethrin; Dustability; Edifenphos; Endosulfan; Endrin; enilconazol; Epichlorhydrin; Epoxiconazole; EPTC; Erichrome; Esfenvalerate; Ethephon; Ethiofencarb; Ethion; Ethirimol; Ethofumesate; ethoprofos; ethyl 3-(n-n-butyl-n-acetyl)aminopropion; ethyleneoxide; Ethylenediamine tetraacetic acid; Etofenprox; etridiazole; etrimfos; ETU; famoxadone; fenamidone; fenamifos; fenarimol; Fenbutatin oxide; fenchlorazole-ethyl; fenhexamide; Fenitrothion; fenmedifam; Fenobucarb; Fenoprop; fenothrin; fenoxaprop-p-ethyl; fenoxycarb; fenpiclonil; fenpropathrin; fenpropidin; Fenpropimorph; Fensulfothion; Fenthion; Fentin; Fentin acetate; Fentin hydroxide; Fenvalerate; ferri phosphate; Ferroin sulphate; ferrosulfate; Fipronil; flocoumafen; florasulam; Fluazifop-butyl; Fluazifop-P-butyl; fluazinam; flucycloxuron; fludioxonil; flufenacet; Fluometuron; fluorglycofen-ethyl; fluoxastrobin; flurenol; fluroxypyr; Flusilazole; flutolanil; Folpet; fonofos; foramsulfuron; Formaldehyde; Formothion; fosalon; fosetyl-aluminium; fosfamidon; fosmet; fosthiazate; foxim; fuberidazole; furalaxyl; furathiocarb; gibbereline; gibberella; Glufosinate; glufosinate-ammonium; glutaraldehyde; glycolbromoacetate; glyphosate-trimesium; Glyphosate; guazatine; haloxyfop-ethoxyethyl; haloxyfop-p-methyl; heptenofos; Hexadecanoic acid; Hexazinone; hexythiazox; fenoxacrim; hydramethylnon; Hydrogen sulphide; Hydroxylammonium chloride; hymexazole; Icaridin; Imazalil; imazamethabenz-methyl; Imidacloprid; indoxacarb; iodosulfuron-methyl-sodium; ioxynil; iprodion; isofenphos; isoproturon; isoxaflutole; iodofore; kasugamycine; kresoxim-methyl; lambda-Cyhalothrin; lenacil; lindane; linuron; magnesiumphosphide; malathion; maleine hydrazide; mancozeb; maneb; MCPA; m-Cresol; mecoprop; mecoprop-p; mepanipyrim; mesotrione; metalaxyl; metalaxyl-m; metaldehyde; metamitron; metam-sodium; metarhizium anisopliae; metazachlor; methabenzthiazuron; methamidophos; methidathion; methiocarb; methomyl; methoprene; methoxyfenozide; methylbromide; methylenebisthiocyanate; methylnaftylaceetamide; methylnaftylacetic acid; metiram; metobromuron; metolachlor; metoxuron; metribuzin; metsulfuron-methyl; mevinphos; milbemectin; molinate; monobromoacetic acid; monocarbamide-dihydrogensulfate; monolinuron; monuron; myclobutanil; N-(2-ethylhexyl)-8,9,10-tribomene-2,3-dicarboxamide; n,n-diallyldichloroaceetamide; sodium bichromate; sodium bisulfite; sodium bromide; sodium chlorite; sodium dichloroisocyanurate; sodium fluoracetate; sodium hydroxide; sodium hypochlorite; sodium octaborate; sodium perborate; sodium-p-toluenesulfonchloramide; nicosulfuron; nitrothal-isopropyl; n-octylbicycloheptenedicarboximide; nonylfenol ethoxylate; nuarimol; O,O-Dimethyl methylphosphoroamidothioate; O,O-Dimethyl phosphoroamidothioate; O,O-Dimethyl S-methylcarbamoylmethylphosphorodithioate; O,S-Dimethyl methylphosphoroamidothioate; O,S-Dimethyl4-nitrophenylphosphorothioate; o-Cresol; octanoic acid; octylfenoxypolyethoxyethanol ; octylisothiazolin-3-on; omethoate; oxadixyl; oxamyl; oxy-demeton-methyl; paclobutrazol; paecilomyces fumosoroseus; paraformaldehyde; paraquat; paraquat-dichloride; parathion (ethyl); parathion-methyl; p-chloro-m-cresol; p-Cresol; penconazole; pencycuron; pendimethalin; permethrin; phenoxyalkanoic herbicides; p-hydroxyphenylsalicylamide; picloram; picoxystrobin; piperonylbutoxide; pirimicarb; pirimiphosethyl; pirimiphos-methyl; poly[oxyethylene(dimethyliminio)ethylene; polybutenen; Potassium bichromate; Potassium bifluoride; Potassium hydroxide; Potassium-n-methyldithiocarbamate; prochloraz; procymidon; profam; prohexadione-calcium; prometryn; propachlor; propamocarb-hydrochloride; propaquizafop; propetamphos; propham; propiconazole; propoxur; propyzamide; prosulfocarb; prothioconazole; pymetrozine; pyraclostrobin; pyrazophos; pyrethrinen; pyridaben; pyridate; pyrifenox; pyrimethanil; pyriproxyfen; quinmerac; quinoclamin; quinoxyfen; quizalofop-ethyl; quizalofop-p-ethyl; rape seed oil; rimsulfuron; salicylic acid; sethoxydim; simazine; s-methoprene; s-metolachlor; spinosad; spirodiclofen; spiromesifen; streptomyces griseoviridis; streptomycine-sulfate; sulcofuron; sulcotrione; sulfotep; Sulphur; tebuconazole; tebufenpyrad; teflubenzuron; tefluthrin; temephos; tepraloxydim; terbufos; terbuthylazine; terbutryn; tetra-acetylethylenediamine; tetrachlorvinfos; tetradifon; tetramethrin; thiabendazol; thiacloprid; thiamethoxam; thifensulfuron; Thiobencarb; thiocyclam hydrogeneoxalate; thiodicarb; thiofanate-methyl; thiometon; thiram; thiuram disulphide; tolclofos-methyl; tolylfluanid; transfluthrin; triadimefon; triadimenol; tri-allate; triazamate; triazophos; tributyltinacrylatecopolymer; tributyltinfluoride; tributyltinphosphate; tributyltinmethacrylate; tributyltinoxide; trichlorfon; trichlorisocyanuric acid; trichoderma harzianum rifai t-22; triclopyr; tridemorf; triphenyltinfluoride; trifloxystrobin; triflumizol; triflumuron; trifluralin; triflusulfuron-methyl; triforine; trinexapac-ethyl; urea herbicides; validamycine; vamidothion; verticillium dahliae kleb.; verticillium lecanii; saturated fatty acids; vinclozolin; warfarin; hydrogenperoxide; Silverthiosulfate; zineb; zincborate; zincnaftenate; zincoxalate; zincoxide; zincpyrithione; zincsilicofluoride; ziram; γ-Chlorophosphamidon and the like.

To ensure that the granular agrochemical composition releases essentially all of its active ingredient (ie, greater than 90% and, preferably, greater than 99%), the core material should release slower than the active ingredient. Otherwise, residues of active ingredient would remain in the controlled release system after complete release of the core material.

In a preferred embodiment of the present invention, the granular core material employed for preparing the compositions is at least partially water soluble and may comprise any of a variety of well known, standard NPK or other such fertilizer granules such as those described in European Community Regulation (EC) No. 2003/2003. Alternatively, the core material may be a water-soluble salt or other such material, e.g. sodium-salts or calcium-salts.

Also, other non-ionic materials may be suitable for use in forming the core of the present compositions, particularly, those which can provide osmotic pressure when dissolved. Examples, of such materials are sugar and urea granules.

Typically, the materials for use in forming the core for the compositions of this invention should have a solubility of about 2 to about 800 g/l, preferably, about 120-450 g/l. Also, the core material should be shaped as a granule having a diameter of about 0.35 to about 6 mm, preferably, about 0.72-4 mm for better distribution of the product.

Preferably, the wax material to be employed for use in preparing the first coating layer should have a melting point between about 50° C. and the degradation temperature of the active ingredient or core material, preferably above about 80° C. The wax can be hydrophobic or hydrophillic.

Exemplary of suitable waxes for use herein are higher alkenes; stearamides; polyolefines such as polyethylene, oxidized polyethylenes, polypropylene, polyisobutylene, styrene-based polymers; (block) copolymers of polyolefines; polyesters; (block) copolymers of polyesters; polyethers, e.g. poly(ethylene oxide), poly(propylene oxide); (block) copolymers of polyethers; vinyl resins such as poly(vinyl acetate), poly(vinyl alcohol), poly(vinyl chloride), poly(vinylidene chloride), poly(vinyl pyrrolidone), poly(vinyl acetal), poly(vinyl methylacetamide); acrylic polymers; cellulose derivatives, e.g. celluloseacetate; polyamides; polyamines; polyimides; polycarbonates; polysulfones; polysulfides; polysaccharides. Also blends of these waxes can be used.

In a further preferred embodiment of this invention the biologically active ingredient or plant protection product for incorporation in the wax to form the first coating layer should be selected from the group consisting of insecticides, herbicides, fertilizers, growth regulators, pheromones, biostimulants, acaricides, miticides, nematocides, fungicides and mixtures thereof and the like.

The controlled release systems of this invention enable economical application of a total amount of active ingredient necessary for season long control without increased risk of leaching, phytotoxicity for crops and is safe for users. The active ingredient is applied without the use of a solvent. Thus, low-solubility active ingredients can be used. Significantly, the system is efficient. At most, only very limited amounts, preferably less than about 10% by weight and, most preferably, less than about 1% by weight, of the active ingredient should be left inside the system.

In order to achieve the high efficiency of release characteristics of the compositions of the present invention, it is preferred to adjust the water-solubility of the core material to correspond to the water-solubility of the active ingredient. When the core material-solubility is too high compared to the active ingredient-solubility, all of the core-material may be released before the release of all the active ingredient. This results in residue of active ingredient in the granules which is not desirable from an environmental and commercial point of view. If the solubility of the core material is too low compared to the solubility of the active ingredient, too much of the core material may be left in the composition after the release of the active. This results in an inefficient use of the core material.

The solubility of the active ingredient and core material may be influenced by additives, such as ionic or non-ionic surfactants, water-soluble polymers or complexing agents. Not all active ingredients demonstrate good water-solubility. Increasing the solubility of an active ingredient, for example, by using a non-ionic surfactant for the active ingredient application renders the actives more soluble and may make the compositions of this invention more widely applicable. Not only the solubility of the core material but, also, the dissolving rate of the core material versus the active ingredient should be considered in formulating the compositions of this invention. Typically, the ratio of core material to active ingredient should be about 1000 to about 0.1 and, preferably, about 200-10. After the release period, less than about 10%, preferably, less than 1% of the initial amount of active ingredient should be present inside the controlled release system. To achieve the desired release longevity of the compositions of this invention, the coating thickness employed should be matched with the solubility of the core material and the active ingredient.

Furthermore, it should be noted that the longevity of release of the active ingredients of the present compositions can be modified by varying the amount of polymeric coating employed. Alternatively, the water-permeability of the polymer coating can be changed. The polymer coating layer can be formed from any (semi-)water-permeable polymeric material, including copolymers, known in the art such as known thermosetting resins, thermoplastic resins and other polymeric materials or latex polymers and mixtures thereof The polymer coating enables slow release of the active ingredient over a period of about 6 to about 104 weeks, preferably, about 3-6 months.

Exemplary of suitable polymers for use in the present invention are such thermoplastic coating materials as vinyl resins such as poly(vinyl acetate), poly(vinyl alcohol), poly (vinyl chloride), poly(vinylidene chloride), poly(vinyl pyrrolidone), poly(vinyl acetal), poly(vinyl methylacetamide); polyolefines such as polyethylene, polypropylene, polyisobutylene; styrene-based polymers; acrylic polymers; polyesters such as poly(alkylene terephthalate), poly(caprolactone); poly(oxy alkylene)s, such as poly(ethylene oxide), poly(propylene oxide); cellulose derivatives, such as celluloseacetate; polyamides;polyamines; polycarbonates; polyimides; polysulfones; polysulfides; polysaccharides and the like.

Suitable thermosetting polymeric coating materials for use herein include polyesters such as alkyds or modified alkyds; epoxy resins; urethane resins; and aminoplastics.

In a most preferred embodiment of this invention, the polymeric composition for use in forming the second coating layer comprises a dicyclopentadiene ("DCPD") polymeric product (containing either linseed oil or an alkyd resin based on a soybean oil) such the polymer coatings employed to produce such fertilizers as those sold by the Scotts Company under the trademark Osmocote® as disclosed in U.S. Pat. Nos. 3,223,518 and 4,657,576.

In preparing the present compositions, the active ingredient is applied onto the granular core material with a wax. Preferably the active ingredient/wax combination is a solid at room temperature and it is applied onto the granular core material as a liquid. The active ingredient can be mixed with a (molten) wax and applied drop wise or sprayed onto the granular material. The active ingredient does not need to dissolve. The mixture of active ingredient and wax can be applied as a dispersion. In addition, functional additives such as surfactants, which are used to modify the water solubility, can be applied with the active ingredients. The use of ionic or non-ionic surfactants enables use of active ingredients in the present compositions that have a low solubility in water, thus, broadening their applicability. Also, waxes that are non-ionic surfactants can be used herein.

The present invention encompasses both granular controlled release agrochemical compositions and processes for the preparation thereof and addresses the problems encountered with regard to functionality of prior compositions in terms of active ingredient release over an extended period of time.

The compositions and processes of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

A sample of the granular agrochemical compositions of the present invention was prepared employing an 0-2-40 fertilizer granule obtained from The Scotts Company (Howden, UK) as the granular core material. This granular core was predominantly composed of potassium sulfate. The sample composition was prepared by initially heating 50 g of the 0-2-40 fertilizer granules (1.7-2.0 mm) in a rotating drum to 110° C. Then, 0.75 g of a non-ionic surfactant wax (a polyethyleneglycol-block-polyethylene, cas nr.: [251553-55-6], hydroxyl number 52.00 mg KOH/g, containing 20% (by weight) polyethylene glycol, obtained from Sigma-Aldrich), was melted and 0.25 g of a biologically active ingredient (imidacloprid, obtained from Sigma-Aldrich) was mixed into in the molten wax.

Then, the resulting mixture of imidacloprid and wax was added to the warm fertilizer (potassium sulfate) granules to form a coating layer on the granular core. The granules with the imidacloprid and wax coating thereon were allowed to cool to room temperature. Subsequently, a second coating layer was applied over the imidacloprid and wax coating layer according to the following procedure. The active-impregnated granules were heated 15 minutes in a rotating flask in an oil-bath at 95° C. A modified unsaturated oil copolymer based alkyd resin sold under the trade name Necolin S9363 by Ashland-Sudchemie-Kernfest GmbH, Germany, was added to the warm granules over a 40 minute period. The solid content of the added resin was 40%. White spirit was used as a solvent and a drier was used to enhance the curing. During the process of applying the second polymer coating layer, air was purged through the system to evaporate the solvent from the resin. After coating 5.5 pph (parts per hundred by weight) on the granular composition having the first coating layer thereon, the resulting composition was cooled to room temperature and was ready for testing. The imidacloprid concentration in this composition was 0.30% by weight as determined by standard High Performance Liquid Chromatography chemical analytical analysis techniques.

The test sample of this Example 1 was subjected to release testing wherein the release of the active ingredient from the coated granular composition was evaluated in water in a so-called waterleach test. For this waterleach test, 200 ml of water was added to 10 g of the coated granular composition. Then the sample was stored at 21° C. and the water was replaced completely with fresh water after 1 day and at weekly intervals thereafter. The removed water was analyzed on active ingredient content with standard analytical methods. For example, the imidacloprid active ingredient release from the test samples of Example 1 was analyzed with HPLC, column: inertsil ODS-2 150×4.6 mm, eluens acetonitrile/water (pH=3 with phosphoric acid).

The release profile was calculated from the initial active ingredient concentration in the granule. The core dissolution was calculated from the measured conductivity. The measured conductivity can be translated into a total amount of nutrients released using the appropriate calibration constants. These calibration constants are specific for a particular type of fertilizer and are determined experimentally.

Figure 1:
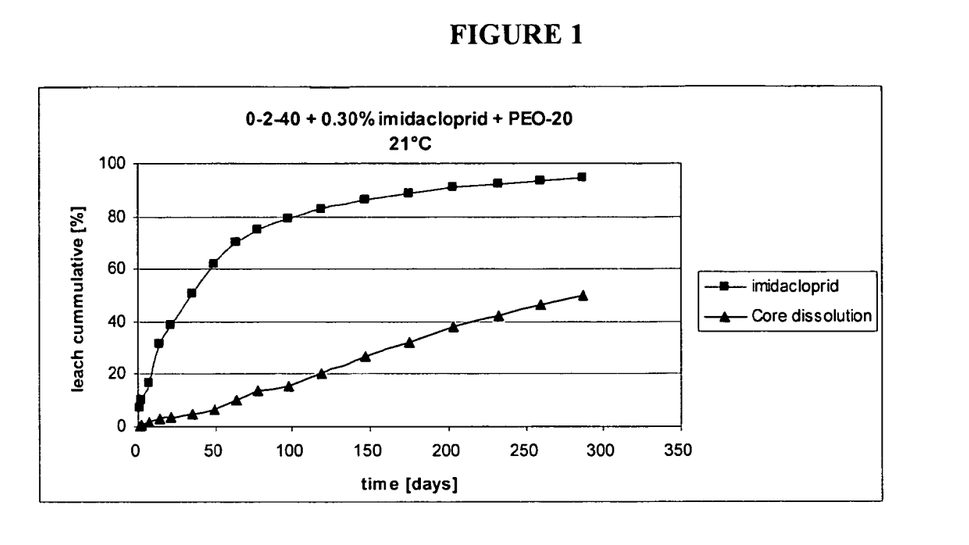
FIG. 1 illustrates the release rate of a granular agrochemical composition of the present invention.

The result of this analytical evaluation was graphed on the basis of percentage release of active ingredient versus percentage release of water soluble core material over a time period up to 287 days as illustrated in FIG. 1. As can be seen from the graphic display in FIG. 1, the granular composition having the biologically active imidacloprid ingredient incorporated into the non-ionic surfactant wax provided an effective and efficient system for release of the active ingredient over a period of greater than 30 days. In fact, as demonstrated by the results shown in FIG. 1, the compositions of this invention provided a release of about 95% (by weight) of the active ingredient over a period of 287 days from the date of initial exposure to moisture while about only about 50% (by weight) of the core material was released over that same time period so that about 50% (by weight) of the water soluble portion of the granular core material remained within the granular composition over the 287 day duration.

EXAMPLE 2

The composition produced in accordance with this Example 2 is distinguishable from the compositions produced in accordance with Example 1 in regard to the wax material employed in forming the first coating layer of test sample of the granular agrochemical composition of the present invention. The procedure used to produce the test sample of this Example 2 was in accordance with the process of Example 1.

Specifically, an 0-2-40 fertilizer granule obtained from The Scotts Company which was predominantly composed of potassium sulfate was employed as the granular core material for the sample composition which was prepared by initially heating 50 g of the 0-2-40 fertilizer granules (1.7-2.0 mm) in a rotating drum to 110° C. Then, 0.75 g of a polyethyleneglycol-block-polyethylene, cas nr.: [97953-22-5], hydroxyl number 55.00 mg KOH/g, containing 50% (by weight) polyethylene glycol, obtained from Sigma-Aldrich) was melted and 0.25 g of a biologically active ingredient (imidacloprid, obtained from from Sigma-Aldrich) was mixed into the molten wax. This wax differed from the wax employed in Example 1 but possessed similarly suitable surfactant characteristics for the imidacloprid biologically active ingredient which was incorporated by mixing into in the molten wax as described in Example 1.

Then, the resulting mixture of imidacloprid and wax was added to the warm fertilizer (potassium sulfate) granules to form a coating layer on the granular core. The granules with the imidacloprid and wax coating thereon were allowed to cool to room temperature. Subsequently, the same polymeric second coating layer as described in Example 1 was applied over the imidacloprid and wax coating layer employing the same procedure as in Example 1 to produce the granular composition for testing. The imidacloprid concentration in the composition of this Example 2 was 0.22% (by weight) as determined by standard High Performance Liquid Chromatography chemical analytical analysis techniques.

Figure 2:
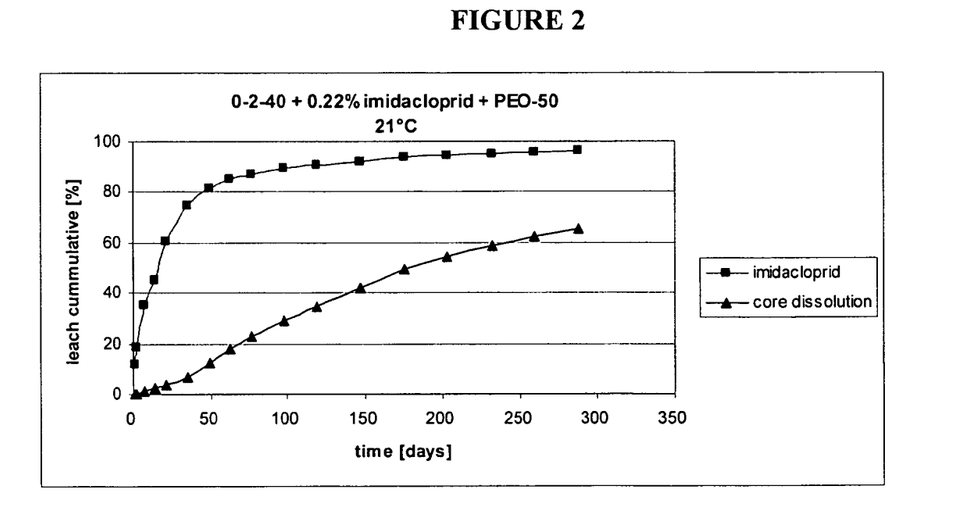
FIG. 2 illustrates the release rate of another embodiment of the granular agrochemical compositions of the present invention.

The composition of this Example 2 was subjected to the release testing procedure as described in Example 1 and the results of this testing is illustrated in FIG. 2. As can be seen from the graphic display in FIG. 2, this granular composition having the biologically active imidacloprid ingredient incorporated into the wax provided an effective and efficient system for release of the active ingredient over a period of greater than 30 days. In fact, as demonstrated by the results shown in FIG. 2, the composition of this invention provided a release of about 96% (by weight) of the active ingredient over a period of 287 days from the date of initial exposure to moisture while only about 65% (by weight) of the core material was released over that same time period so that about 35% (by weight) of the water soluble portion of the granular core material remained within the granular composition over the 287 day duration.

EXAMPLE 3

The composition produced in accordance with this Example 3 is distinguishable from the compositions produced in accordance with Example 2 in regard to the amount of the active ingredient which was incorporated into the wax material in forming the first coating layer of test sample of the granular agrochemical composition of the present invention.

The procedure used to produce the test sample of this Example 3 was in accordance with the process of Example 1. Specifically, an 0-2-40 fertilizer granule obtained from The Scotts Company which was predominantly composed of potassium sulfate was employed as the granular core material for the sample composition which was prepared by initially heating 50 g of the 0-2-40 fertilizer granules (1.7-2.0 mm) in a rotating drum to 110° C. Then, 0.75 g of a polyethyleneglycol-block-polyethylene, cas nr.: [97953-22-5], hydroxyl number 55.00 mg KOH/g, containing 50% polyethyleneglycol, obtained from Sigma-Aldrich) was melted and 0.75 g of a biologically active ingredient (imidacloprid, obtained from Sigma-Aldrich) was mixed into the molten wax. This amount of biologically active ingredient is higher than the amount used in Example 2.

Then, the resulting mixture of imidacloprid and wax was added to the warm fertilizer (potassium sulfate) granules to form a coating layer on the granular core. The granules with the imidacloprid and wax coating thereon were allowed to cool to room temperature. Subsequently, the same polymeric second coating layer as described in Example 1 was applied over the imidacloprid and wax coating layer employing the same procedure as in Example 1 to produce the granular composition for testing. The imidacloprid concentration in the composition of this Example 3 was 0.95% by weight as determined by standard High Performance Liquid Chromatography chemical analytical analysis techniques.

Figure 3:
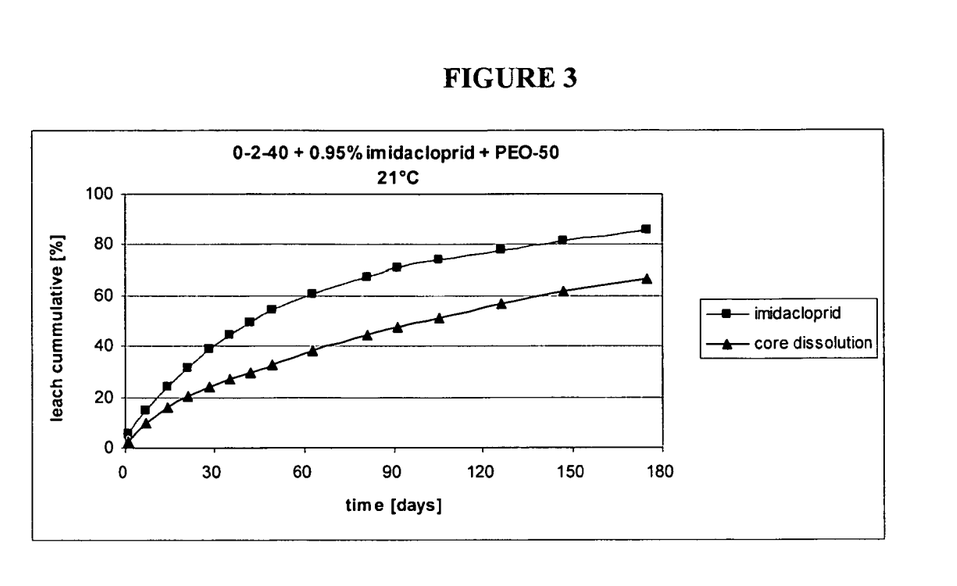
FIG. 3 illustrates the release rate of a another embodiment of the granular agrochemical compositions of the present invention.

The composition of this Example 3 was subjected to the release testing procedure as described in Example 1 and the results of this testing is illustrated in FIG. 3. As can be seen from the graphic display in FIG. 3, this granular composition having the biologically active imidacloprid ingredient incorporated into the wax provided an effective and efficient system for release of the active ingredient over a period of greater than 30 days. In fact, as demonstrated by the results shown in FIG. 3, the composition of this invention provided a release of about 86% (by weight) of the active ingredient over a period of 175 days from the date of initial exposure to moisture while only about 67% (by weight) of the core material was released over that same time period so that about 33% (by weight) of the water soluble portion of the granular core material remained within the granular composition over the 175 day duration.

EXAMPLE 4

The composition produced in accordance with this Example 4 is distinguishable from the compositions produced in accordance with Example 1 in regard to the active ingredient which was incorporated into the wax material in forming the first coating layer of test sample of the granular agrochemical composition of the present invention and in regard to polymer composition which was employed in forming the second coating layer on the compositions. The procedure used to produce the test sample of this Example 4 was in accordance with the process of Example 1.

Specifically, an 0-2-40 fertilizer granule obtained from The Scotts Company which was predominantly composed of potassium sulfate was employed as the granular core material for the sample composition which was prepared by initially heating 50 g of the 0-2-40 fertilizer granules (1.7-2.0 mm) in a rotating drum to 110° C. Then, 3.5 g of the non-ionic surfactant wax of Example 1 (a polyethyleneglycol-block-polyethylene, cas nr.: [251553-55-6], hydroxyl number 52.00 mg KOH/g, containing 20% by weight polyethyleneglycol, obtained from Sigma-Aldrich), was melted and 3.5 g of a Fosetyl-Aluminum biologically active ingredient obtained from Bayer CropSciences was incorporated by mixing into the molten wax by the same procedure described in Example 1.

Then, the resulting mixture of Fosetyl-Aluminum and wax was added to the warm fertilizer (potassium sulfate) granules to form a coating layer on the granular core. The granules with the Fosetyl-Aluminum and wax coating thereon were allowed to cool to room temperature. Subsequently, a polymeric second coating layer was applied over the Fosetyl-Aluminum and wax by the process described in Example 1 to produce the granular composition for testing. The polymer employed as the second coating layer was a modified unsaturated oil copolymer based alkyd resin sold under the trade name Necolin 4071 by Ashland-Sudchemie-Kernfest GmbH, Germany. The Fosetyl-Aluminum concentration in the composition of this Example 4 was 4.75% (by weight) as determined by standard High Performance Liquid Chromatography chemical analytical analysis techniques.

Figure 4:
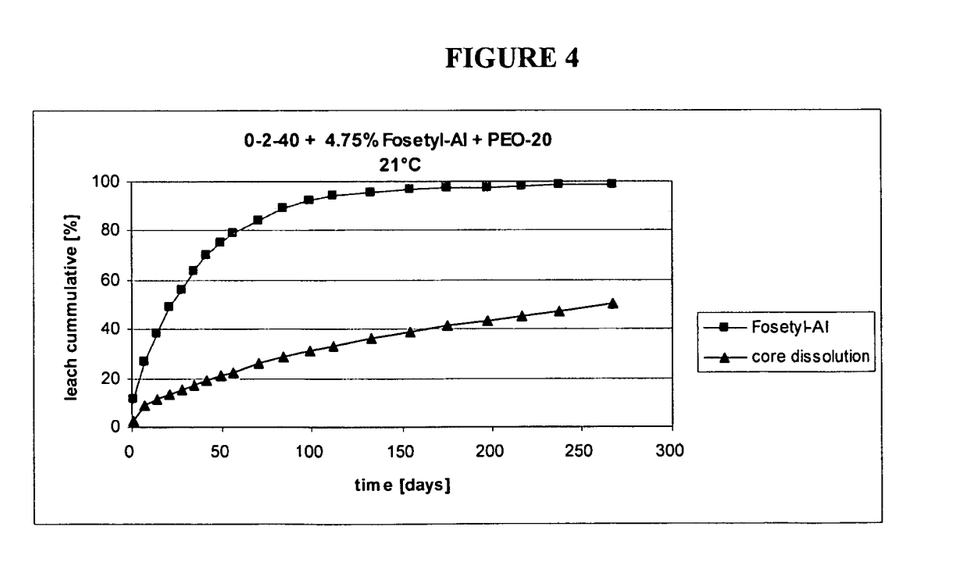
FIG. 4 illustrates the release rate of another embodiment of the granular agrochemical compositions of the present invention.

The composition of this Example 4 was subjected to the release testing procedure as described in Example 1 except that the Fosetyl-Aluminium release was analyzed with ion-chromatography column: Phenomenex starion A300: 1050× 4.6 mm, eluens 5% acetone in water, with 1 mM HNO3 and 3 mM NaNO$_3$ and the results of this testing is illustrated in FIG. 4. As can be seen from the graphic display in FIG. 4, this granular composition having the biologically active Fosetyl-Aluminum ingredient incorporated into the wax provided an effective and efficient system for release of the active ingredient over a period of greater than 30 days. In fact, as demonstrated by the results shown in FIG. 4, the composition of this invention provided release of 99% (by weight) of the active ingredient over a period of about 267 days from the date of initial exposure to moisture while only about 50% (by weight) of the core material was released over that same time period.

EXAMPLE 5

Another granular test sample compositions in accordance with this invention was produced utilizing a hydrophobic wax material in forming the first coating layer. The procedure used to produce the test sample of this Example 5 was in accordance with the process of Example 1.

Specifically, an 0-2-40 fertilizer granule obtained from The Scotts Company which was predominantly composed of potassium sulfate was employed as the granular core material for the sample composition which was prepared by initially heating 50 g of the 0-2-40 fertilizer granules (1.7-2.0 mm) in a rotating drum to 110° C. Then, 2.5 g of a hydrophobic wax (Novoflow 02102 obtained from Holland Novochem BV, Nieuwegein, the Netherlands)—was melted and 2.5 g of a Fosetyl-Aluminum biologically active ingredient obtained from Bayer CropSciences was incorporated by mixing into the molten wax by the same procedure described in Example 1.

Then, the resulting mixture of Fosetyl-Aluminum and wax was added to the warm fertilizer (potassium sulfate) granules to form a coating layer on the granular core. The granules with the Fosetyl-Aluminum and wax coating thereon were allowed to cool to room temperature. Subsequently, a polymeric second coating layer was applied over the Fosetyl-Aluminum and wax by the process described in Example 1 to produce the granular composition for testing. The polymer employed as the second coating layer was a modified unsaturated oil copolymer based alkyd resin sold under the trade name Necolin 4071 by Ashland-Sudchemie-Kernfest GmbH, Germany. The Fosetyl-Aluminum concentration in the composition of this Example 5 was 3.5% by weight as determined by standard High Performance Liquid Chromatography chemical analytical analysis techniques.

Figure 5:
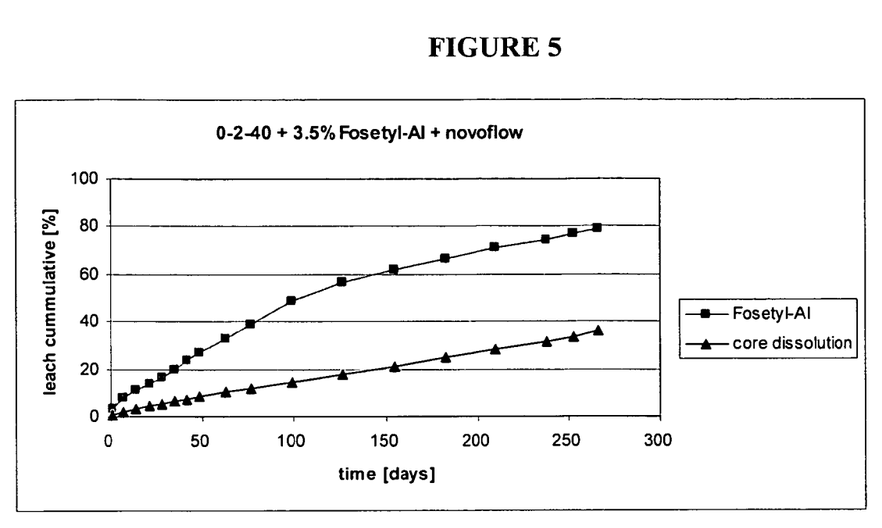
FIG. 5 illustrates the release rate of another embodiment of the granular agrochemical compositions of the present invention.

The composition of this Example 5 was subjected to the release testing procedure as described in Example 1 as modified in Example 4 and the results of this testing is illustrated in FIG. 5. As can be seen from the graphic display in FIG. 5, this granular composition having the biologically active Fosetyl-Aluminum ingredient incorporated into the hydrophobic wax provided an effective and efficient system for release of the active ingredient over a period of greater than 30 days. In fact, as demonstrated by the results shown in FIG. 5, the composition of this invention provided release of about 80% (by weight) of the active ingredient over a period of about 266 days from the date of initial exposure to moisture while only about 36% (by weight) of the core material was released over that same time period so that about 64% (by weight) of the water soluble portion of the granular core material remained within the granular composition over the approximately 266 day duration. This result demonstrates the benefits derived from employing a hydrophobic wax resulting in a slower releasing product which is desirable when a highly soluble active ingredient is incorporated therein.

Although the invention has been described in its preferred forms with a certain degree of particularity, it is to be understood that the present disclosure has been made by way of example only. Those skilled in the art will recognize, or be able to ascertain using no more than routine experimentation, many equivalents to the specific embodiments of the invention described herein. Such equivalents are intended to be encompassed within the scope of the following claims.

All publications, patents and patent applications mentioned in this specification are herein incorporated by reference into the specification to the same extent as if each individual publication, patent or patent application was specifically and individually indicated to be incorporated herein by reference.

The invention claimed is:

1. A granular composition comprising:
    a granular core material comprising a water soluble material and having a diameter of about 0.35 to about 6 mm;
    a first coating layer on the surface of the core material, wherein:
        said first coating layer comprises a wax material and a biologically active ingredient incorporated in the wax material, wherein the wax material comprises a higher alkene wax, a stearamide wax, a polyolefin wax, a styrene-based polymer wax, a block copolymer of a polyolefin wax, a polyester wax, a block copolymer of polyester wax, a polyether wax, a block copolymer of a polyether wax, a vinyl resin wax, an acrylic polymer wax, a polyamine wax, or a combination thereof; and
    a second coating layer on the surface of the first coating layer, wherein the second coating layer comprises a polymeric composition comprising a polyester, an epoxy resin, a urethane resin, or an aminoplastic;
    wherein:
    the core material is adapted to generate sufficient osmotic pressure within the granular composition to cause the biologically active ingredient in the first coating layer to be released therefrom when the composition is contacted with moisture;
    the second coating layer is structured to withstand the osmotic pressure generated by the core material; and
    said composition is adapted to release the biologically active ingredient at a controlled rate over a period of greater than 30 days from a date of initial exposure of the composition to moisture whereby greater than 90% of the biologically active ingredient incorporated in the wax material of the first coating layer is released at a controlled rate of release from the granular composition over a period of time greater than 30 days and before the granular core material is completely released from the granular composition.

2. The granular composition of claim 1, wherein the core material comprises a fertilizer.

3. The granular composition of claim 2, wherein the fertilizer comprises ammonium sulfate, potassium nitrate, potassium sulfate, urea, ammonium nitrate, ammonium phosphate, super-phosphate, calcium phosphate, potassium phosphate, potassium chloride, magnesium oxide, magnesium sulfate, dolomite, or a mixture thereof.

4. The granular composition of claim 2, wherein the core material further comprises at least one secondary nutrient or micronutrient.

5. The granular composition of claim 4, wherein the secondary nutrient comprises calcium, magnesium, sulfur, or a mixture thereof.

6. The granular composition of claim 4, wherein the micronutrient comprises chelated or non-chelated iron, copper, zinc, manganese, boron, cobalt, molybdenum, or a mixture thereof.

7. The granular composition of claim 1, wherein the biologically active ingredient comprises a pesticide, insecticide, herbicide, fungicide, fertilizer, growth regulator, pheromone, biostimulant, acaricide, miticide, nematocide, or a mixture thereof.

8. The granular composition of claim 1, wherein the wax material has a melting point of greater than 50° C.

9. The granular composition of claim 8, wherein the wax material is hydrophilic.

10. The granular composition of claim 1, wherein the wax material is water soluble.

11. The composition of claim 1, wherein said wax material has a melting point ranging from about 50° C. to the degradation temperature of the active ingredient or core material.

12. The composition of claim 11, wherein said wax material has a melting point above 80° C.

13. The composition of claim 1, wherein the second coating layer is semi-water permeable.

14. The composition of claim 1, wherein the composition is adapted to release the biologically active ingredient at a controlled rate over a period of greater than about 90 days from a date of initial exposure of the composition to moisture.

15. The granular composition of claim 1, wherein the wax material comprises polyethylene wax, polyethylene oxide wax, or a combination thereof.

16. The granular composition of claim 1, wherein the wax material comprises a polyethyleneglycol-block-polyethylene copolymer wax.

17. The granular composition of claim 1, wherein the polymeric composition comprises an alkyd resin.

18. The granular composition of claim 16, wherein the polymeric composition comprises an alkyd resin.

19. The granular composition of claim 1, wherein the second coating layer consists of a polymeric composition consisting of alkyds, modified alkyds, epoxy resins, urethane resins, aminoplastics, or mixtures thereof.

20. The granular composition of claim 1, wherein said biologically active ingredient is fosetyl-aluminum.

21. A process for preparing a granular composition comprising:

providing a granular core material comprising a water soluble material and having a diameter of about 0.35 to about 6 mm;

applying on the surface of the core material a first coating layer comprising a wax material and a biologically active ingredient incorporated in the wax material, wherein the wax material comprises a higher alkene wax, a stearamide wax, a polyolefin wax, a styrene-based polymer wax, a block copolymer of a polyolefin wax, a polyester wax, a block copolymer of polyester wax, a polyether wax, a block copolymer of a polyether wax, a vinyl resin wax, an acrylic polymer wax, a polyamine wax, or a combination thereof; and applying on the surface of the first coating layer a second coating layer comprising a polymeric composition comprising a polyester, an epoxy resin, a urethane resin, or an aminoplastic;

wherein:

the core material is adapted to generate sufficient osmotic pressure within the granular composition to cause the biologically active ingredient in the first coating layer to be released therefrom when the composition is contacted with moisture;

the second coating layer is structured to withstand the osmotic pressure generated by the core material; and the composition is adapted to release the biologically active ingredient at a controlled rate over a period of greater than 30 days from a date of initial exposure of the composition to moisture whereby greater than 90% of the biologically active ingredient incorporated in the wax material of the first coating layer is released at a controlled rate of release from the granular composition over a period of time greater than 30 days and before the granular core material is completely released from the granular composition.

* * * * *